US007402136B2

United States Patent
Hossack et al.

(10) Patent No.: US 7,402,136 B2
(45) Date of Patent: Jul. 22, 2008

(54) EFFICIENT ULTRASOUND SYSTEM FOR TWO-DIMENSIONAL C-SCAN IMAGING AND RELATED METHOD THEREOF

(75) Inventors: John A. Hossack, Charlottesville, VA (US); William F. Walker, Earlysville, VA (US); Travis N. Blalock, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 79 days.

(21) Appl. No.: 10/542,242

(22) PCT Filed: Jan. 15, 2004

(86) PCT No.: PCT/US2004/001002

§ 371 (c)(1),
(2), (4) Date: Jul. 14, 2005

(87) PCT Pub. No.: WO2004/065978

PCT Pub. Date: Aug. 5, 2004

(65) Prior Publication Data

US 2006/0052697 A1    Mar. 9, 2006

Related U.S. Application Data

(60) Provisional application No. 60/440,262, filed on Jan. 15, 2003.

(51) Int. Cl.
*A61B 8/00* (2006.01)
(52) U.S. Cl. ....................................... 600/447

(58) Field of Classification Search ......... 600/443–447; 128/916; 73/625–626
See application file for complete search history.

(56) References Cited

U.S. PATENT DOCUMENTS

| 4,275,461 A | | 6/1981 | Sternick et al. | |
|---|---|---|---|---|
| 4,694,434 A | * | 9/1987 | von Ramm et al. | 367/7 |
| 5,469,851 A | | 11/1995 | Lipschutz | |
| 5,997,479 A | * | 12/1999 | Savord et al. | 600/447 |
| 6,048,316 A | * | 4/2000 | Zhao et al. | 600/447 |
| 6,276,211 B1 | | 8/2001 | Smith | |
| 6,537,219 B2 | * | 3/2003 | Poland et al. | 600/447 |
| 6,572,547 B2 | * | 6/2003 | Miller et al. | 600/437 |
| 2002/0144549 A1 | | 10/2002 | Yao | |

FOREIGN PATENT DOCUMENTS

DE    19524505 A1    11/1996

* cited by examiner

*Primary Examiner*—Francis J. Jaworski
(74) *Attorney, Agent, or Firm*—Robert J. Decker

(57) ABSTRACT

An ultrasound system and related method for forming 2D C-scan images and/or collecting 3D image data from 2D transducer arrays. The system including in part a 2D transducer array of elements, transmit voltage generation means for each element, a memory buffer with or part of channels for each element, and a receive beamformer. On a time serial or sequential basis, several times for each line of firing, the contents of the per element memory buffer are read into the beamformer with different focusing values for each buffer reading cycle. In this way, the beamformer can calculate beamformed image values for multiple points per line firing cycle—or per each line of signals between the transducer array and receive beamformer.

29 Claims, 6 Drawing Sheets

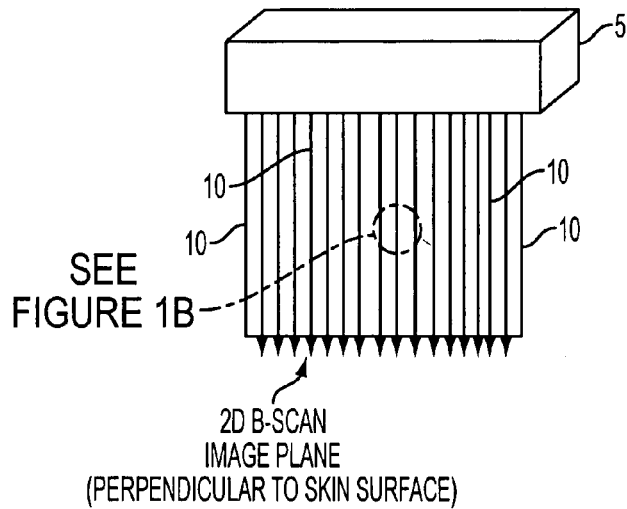
SEE
FIGURE 1B
2D B-SCAN
IMAGE PLANE
(PERPENDICULAR TO SKIN SURFACE)
FIG. 1A
PRIOR ART
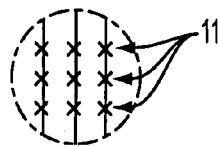
FIG. 1B
PRIOR ART
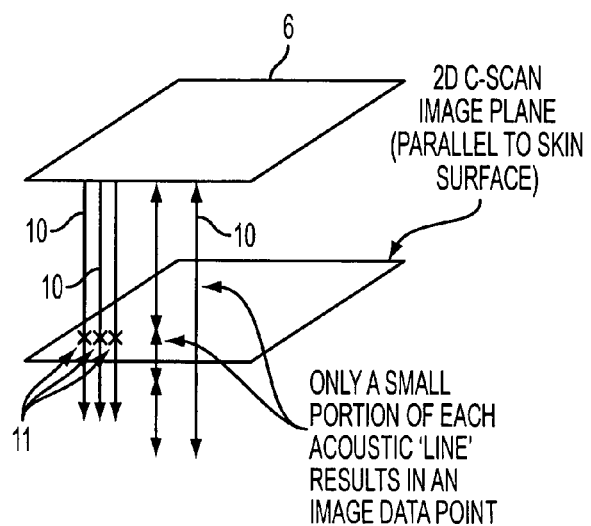
2D C-SCAN
IMAGE PLANE
(PARALLEL TO SKIN
SURFACE)
ONLY A SMALL
PORTION OF EACH
ACOUSTIC 'LINE'
RESULTS IN AN
IMAGE DATA POINT
FIG. 2
PRIOR ART

EFFICIENT ULTRASOUND SYSTEM FOR TWO-DIMENSIONAL C-SCAN IMAGING AND RELATED METHOD THEREOF

CROSS-REFERENCES TO RELATED APPLICATIONS

This application is a national stage filing of International Application No. PCT/US2004/001002, filed on Jan. 15, 2004, which claims benefit under 35 U.S.C Section 119(e) from U.S. Provisional Application Ser. No. 60/440,262, filed Jan. 15, 2003, entitled "Efficient Electronic Hardware for C-scan Planes with 2D Arrays in Diagnostic Ultrasound and Related Method Thereof," the entire disclosures of which are hereby incorporated by reference herein in their entirety.

The present application is also related to International Application No. PCT/US03/06607, filed Mar. 6, 2003, entitled "An Intuitive Ultrasonic Imaging System and Related Method Thereof," of which is assigned to the present assignee and is hereby incorporated by reference herein in its entirety. The present invention may be implemented with the technology discussed throughout aforementioned International Application No. PCT/US03/06607.

The present application is also related to PCT International Application No. PCT/US2004/000888, filed Jan. 14, 2004, entitled "Ultrasonic Transducer Drive," of which is assigned to the present assignee and is hereby incorporated by reference herein in its entirety. The present invention may be implemented with the technology discussed throughout aforementioned International Application entitled "Ultrasonic Transducer Drive."

The present application is also related to PCT International Application No. PCT/US2004/000887, filed Jan. 14, 2004, entitled "Ultrasound Imaging Beam-former Method and Apparatus," of which is assigned to the present assignee and is hereby incorporated by reference herein in its entirety. The present invention may be implemented with the technology discussed throughout aforementioned International Application entitled "Ultrasound Imaging Beam-former Method and Apparatus."

FIELD OF THE INVENTION

The present invention relates to ultrasonic imaging, and in particular to two-dimensional C-scan imaging with improved efficiencies and processing capabilities.

BACKGROUND OF THE INVENTION

Ultrasonic imaging is widely used in many settings, including medical applications. Of particular importance is the use of ultrasound data in the study of tissue. Physicians may use acquired ultrasound data to assist guiding a catheter through a patient's body, or to non-invasively locate vessels prior to IV insertions. The insertion of needles may also be further complicated in some people whose veins are not readily apparent from the skin's surface, for example, in people with thick layers of fat or infants whose veins are small and difficult to detect. In other circumstances involving shock, arteries that need to be accessed to sample blood gasses shrink in response and thus become even more difficult to detect. For some situations, it may be necessary to surgically cut through the body in order to access the desired internal features, a process that is risky and may cause unnecessary delays to treatment.

A typical ultrasonic imaging system includes an array of transducers, a transmit beamformer, and a receive beamformer. The transmit beamformer supplies electrical waveform signals to the transducer arrays, which in turn produce associated ultrasonic signals. Structures in front of the transducer arrays scatter ultrasonic energy back to the transducers, which then generates receive electrical signals. The electrical receive signals are delayed for selected times specific to each transducer so that ultrasonic energy scattered from selected regions adds coherently, while ultrasonic energy from other regions does not. Array processing techniques for processing received signals in this way are known as beamforming and are well known to those in the field.

Current low cost ultrasound imaging devices are either mechanically scanned devices or one dimensional (1D) phased arrays, which are single rows of parallel elements spaced in the azimuthal direction. Each of these can produce a B-scan—an image 'slice' that is perpendicular to the face of the transducer and the skin's surface. Beamforming in one dimension can be realized through a relatively straightforward implementation using a linear array of sensors and a beamformiing processor that delays each sensor output by the appropriate amount, weights each sensor output by multiplying by the desired weighting factor, and sums the outputs of the multiplying operation.

While the B-scan can be swept through a volume of tissue and the user can, in principle, visualize the three-dimensional (3D) anatomy, such visualization requires significant training and experience. The C-scan, on the other hand, displays images parallel to the skin's surface, giving the impression of viewing the tissue of interest with the perspective of a clear 'window' through the skin. The two systems are illustrated in FIGS. 1(A)-(B) and 2, which respectively show conventional 2D B-Scan and 2D C-Scan operations. Referring to FIGS. 1(A)-(B), having a 1D array 5 in the B-Scan mode, each fired acoustic line 10 in the B-Scan mode results in a long sequence or 'line' of image data or points 11. However, referring to FIG. 2, in the C-Scan mode, only one image point 11 in the total sequence of points for each line 10 of firing is essentially obtained.

The C-Scan requires the use of a 2D array 6 processing a 3D volume of data. A beamforming processor becomes much more complex when a 2D sensor array is used. Not only does the number of time delay operations increase as the square of the size of the array, but also the physical structures required to connect each sensor to its corresponding delay becomes increasingly complex. The complexity is increased by the need for continuous operation. Conventional ultrasound systems have beamformers that continuously update beamformed received echo data so that images are displayed in "real time," or as the echo signals arrive. Since the speed of sound is slow, it becomes necessary for all imaging data along a particular beam line to be continuously formed for that line, and accordingly, it is generally not acceptable to form images with discrete, fixed receive beamforming (or focusing) parameters through multiple signal transmissions.

The vast majority of ultrasound phased arrays that have been researched and used in industry have been 1D transducer arrays. In recent years, there has been some growth in developments involving 1.5D arrays, which consists of a small number of elements (i.e., frequently less than 8) spaced in the elevation direction. Although work has been performed on 2D arrays, progress has generally proven to be extremely challenging. This results from a combination of fabrication difficulties with the transducers, particularly in the electrical connections, and the cost and bulk of the required beamforming hardware. While the hardware challenge diminishes with improvements in integrated circuits, it is evident that achieving a fully populated 2D array is very challenging.

In summary, there is great interest in producing high quality C-Scan images. However, multi-dimensional ultrasonic systems using the 2D arrays required to produce C-scan images are unrealistically high in implementation complexity, size and cost. Moreover, current multi-dimensional ultrasonic systems typically process full 3D volumes of image data. Lacking in particular is a system that efficiently realizes the unique simplifications possible for 2D C-Scans, for which only one plane of data is required for display, as opposed to a full 3D data set normally acquired using 2D transducer arrays. As illustrated, it is evident from the prior art exemplified in FIG. 2 that a significant portion of the time during acquisition in the C-Scan mode is wasted where the received signals make no contribution to the final image. Thus, the conventional multi-dimensional imaging system potentially wastes considerable processing power in producing C-Scan images, and can realize greater efficiency by appreciating that the final 2D image is limited in its cross sectional volume to a single plane of data.

SUMMARY OF THE INVENTION

The present invention provides a beamforming system and related method for forming 2D C-scan images and/or collecting 3D image data from 2D transducer arrays that result in approximately one order of magnitude reduction, for example but not limited thereto, in processing complexity as compared to conventional beamforming systems.

According to the present invention, the beamforming system comprises a 2D transducer array of elements, transmit voltage generation means for each element, a memory buffer with or part of channels for each element, and a receive beamformer. On a time serial or sequential basis, several times for each line of firing, the contents of the per element memory buffer are read into the beamformer with different focusing values for each buffer reading cycle. In this way, the beamformer can calculate beamformed image values for multiple points per line firing cycle—or per each line of signals between the transducer array and receive beamformer.

Additionally, in exemplary embodiments, receive amplification device for each element, as well as analog to digital converters for each amplifier associated with each element, are employed. Alternative embodiments use charged-coupled devices (CCD), i.e., analog signal storage, instead of analog to digital signal buffers. Moreover, while the present invention allows for a fully populated 2D array, a subset of available elements of the transducer array can be used, if necessary.

Not only does the present invention enable each beamformed line to yield more focused image points per line firing cycle than conventional 2D array systems (which typically only provide one beamformed point per line firing cycle), but considerable time for processing is available in the remainder of time between subsequent firing cycles. One example of additional processing enabled by the present invention system and method is the averaging of signals. The ability to average signals allows for the use of smaller and high-frequency transmit signals, thus further saving processing power. The enhanced processing capabilities also enable the transmit signals to be unfocused, or able to fire several elements of the array at once, instead of focused individually for each element as in conventional systems. A related advantage of the present invention is the ability to use small sizes (i.e., number of bits) for storage devices, thus minimizing hardware size and costs.

In addition, the present invention enables application of various techniques that are known and/or as cited throughout this document. For example, but not limited thereto, spatial and frequency compounding thereby allowing reductions (i.e. allowing improvements) in image speckle with minimal cost in frame rate (i.e., computation) using one technique sometimes known as receive-only compounding. Focus data from different active apertures may be invoked, detected and combined to use the speckle reduced image. Using the present invention this technique can be applied with no cost in image acquisition rate.

In short, the present invention provides a low cost, efficacious means for producing 2D C-scans and/or collecting 3D image data using 2D arrays. The savings may be realized in the form, but not limited thereto, of any desired combination of lower cost, reduced size, enhanced resolution and improved imaging penetration. Unlike prior art systems and conventional beamforming approaches, the present invention can enable commercially feasible 2D array based C-Scan forming ultrasound imaging systems for non-invasively assisting in routine clinical operations other applications as desired or required.

In one aspect, the present invention provides an ultrasonic imaging system capable of producing C-mode images and/or collecting 3D image data of a target (or region of a target). The system comprising: a two-dimensional transducer array comprising a plurality of elements that transmits and receives ultrasound signals; an array of processing channels, wherein the processing channels correspond with the plurality of elements, the processing channels for receiving the receive ultrasound signals; a storage device for receiving the channel signals for storage; and a beamforming device that receives stored data in a time serial manner from the storage device more than once per transmit firing event and forms multiple focused image points arranged on a C-scan plane.

In one aspect, the present invention provides an ultrasonic imaging method capable of producing C-mode images and/or collecting 3D image data of a target (or region of a target). The method comprising: transmitting and receiving ultrasound signals; storing the receive ultrasound data; and receiving the stored data in a beamforming device in a time serial manner, wherein the data is received and beamformed more than once per transmit firing event and forms multiple focused points arranged on a C-scan plane.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which:

FIG. 1(A) schematically illustrates a conventional B-Scan operation, wherein FIG. 1(B) is a magnified partial view of the image points or data of the line shown in FIG. 1(A).

FIG. 2 schematically illustrates a conventional C-Scan operation.

DETAILED DESCRIPTION OF THE INVENTION

Figure 3:
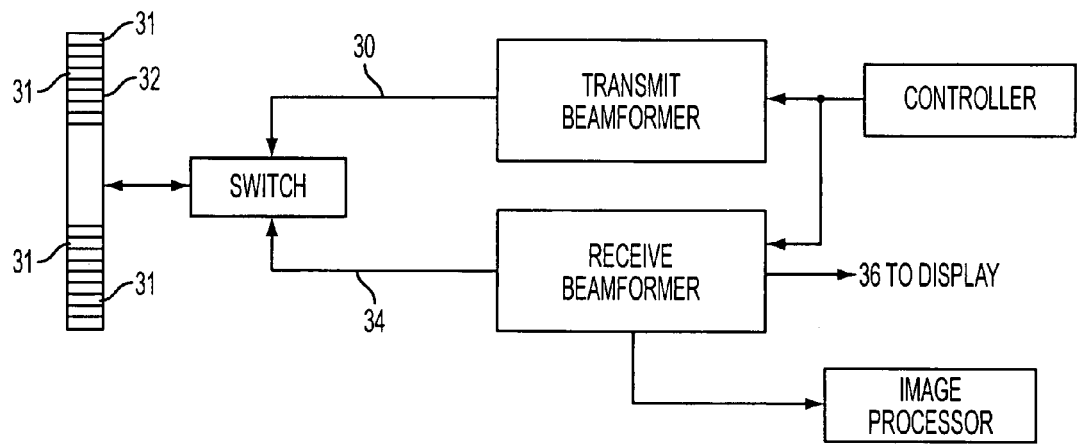
FIG. 3 schematically illustrates a beamforming system.

FIG. 3 illustrates a conventional beamforming system. A transmit generator 30 applies transmit voltage energy signals to an array of transducers 32 having multiple elements 31. The elements 31 of the transducer each receive the transmit electrical signals and generate respective ultrasonic pressure (acoustic) signals. Conventional beamforming operations are applied for each firing of signals. The timing of the firings may be configured to produce one tightly focused beam, multiple transmit beams or may essentially unfocused depending on the beamforming approach being used. For example, a flat, plane wave is used in transmit in the system and method provided in International Application No. PCT/US03/06607, filed Mar. 6, 2003, entitled "An Intuitive Ultrasonic Imaging System and Related Method Thereof," of which is assigned to the present assignee and is hereby incorporated by reference herein in its entirety. Conventional beamforming also involves the procedure of apodization for selectively recovering signals at higher frequencies that are typically lost in low-pass filtering of electronic receivers. Various ultrasound systems are found in the following U.S. Patents and are hereby incorporated by reference herein in their entirety: U.S. Pat. No. 6,669,641 B2 to Poland et al., entitled "Method of and System for Ultrasound Imaging;" U.S. Pat. No. 6,641,534 B2 to Smith et al., entitled "Methods and Devices for Ultrasound Scanning by Moving Sub-Apertures of Cylindrical Ultrasound Transducer Arrays in Two Dimensions;" U.S. Pat. No. 6,582,372 B2 to Poland, entitled "Utrasound System for the Production of 3-D Images;" U.S. Pat. No. 6,491,634 B1 to Leavitt et al., entitled "Sub-Beamforming Apparatus and Method for a Portable Ultrasound Imaging System;" U.S. Pat. No. 6,380,766 B2 to Savord, entitled "Integrated Circuitry for Use With Transducer Elements in an Imaging System;" U.S. Pat. No. 6,276,211 B1 to Smith, entitled "Methods and Systems for Selective Processing of Transmit Ultrasound Beams to Display Views of Selected Slices of a Volume;" U.S. Pat. No. 6,179,780 B1 to Hossack et al., entitled "Method and Apparatus for Medical diagnostic Ultrasound Real-Time 3-D Transmitting and Imaging;" U.S. Pat. No. 6,126,602 to Savord et al., entitled "Phased Array Acoustic Systems With Intra-Group Processors;" U.S. Pat. No. 6,013,032 to Savord, entitled "Beamforming Methods and Apparatus for Three-Dimensional Ultrasound Imaging Using Two-Dimensional Transducer Array;" U.S. Pat. No. 5,997,479 to Savord et al., entitled "Phased Array Acoustic Systems With Intra-Group Processors;" U.S. Pat. No. 4,949,310 to Smith et al., entitled "Maltese Cross Processor: A High Speed Compound Acoustic Imaging System;" U.S. Pat. No. 6,122,223 to Hossack, entitled "Ultrasonic Transmit Waveform Generator;" U.S. Pat. No. 6,122,222 to Hossack et al., entitled "Ultrasonic Transmit and Receive System;" U.S. Pat. No. 5,933,389 to Hossack et al., entitled "Ultrasonic Imaging System and Method;" U.S. Pat. No. 5,619,999 to Von Behren et al., entitled "Body Surface Position Locator for Ultrasound Transducer;" U.S. Pat. No. 5,566,675 to Li et al., entitled "Beamformer for Phase Aberration Correction;" U.S. Pat. No. 5,483,963 to Butler et al., entitled "Two Dimensional Transducer Integrated Circuit;" U.S. Pat. No. 5,447,158 to Nakajima et al., entitled "Ultrasonic Imaging Method and System Capable of Displaying B-Mode Image and Color Flow Mapping Image Over Wide Field;" U.S. Pat. No. 5,063,541 to Kondo et al., entitled "Beam Forming Method and Apparatus Therefore in Ultrasonic Imaging System;" and U.S. Pat. No. 4,694,434 to von Ramm et al., entitled "Three-Dimensional Imaging System."

After the beamformer 34 receives the signals, it subsequently sends beamformed lines to the display 36. Advanced systems may use excess processing power to process the element signals twice, or more, in real time as they arrive, to create more than one focused line per line of firing. However, forming additional lines requires excess hardware or loss of resolution if the processing capability is shared between the tasks of forming different lines. As a practical matter, the system can only form very few focused lines "per line firing cycle"—specifically, for each line of signal transmission spanning the array to the receiver.

Particularly for C-Scan images, each focused pixel spot on the display requires a separate beamforming delay operation (see FIG. 2), although in practice, only a subset of pixels actually undergoes beamforming operations while intervening pixel values are interpolated. However, a modest, reasonable resolution may require at least 50×50=2500 beamforming operations. This should be contrasted with a regular B-Mode scan, which only requires 256 or so beamformed lines (see FIGS. 1(A)-(B)). The C-Scan thus requires considerably more processing power than the B-Scan to retain sufficient resolution. Additionally, time of flight considerations in conventional imaging limit the number of lines per frame to approximately this number (256) if an adequate frame rate (i.e., 30 or more frames per second in cardiology applications) is to be achieved. As a result of these limitations on current C-Scan imaging, a system for forming more than one beamformed point per line of firing is desired.

Figure 4:
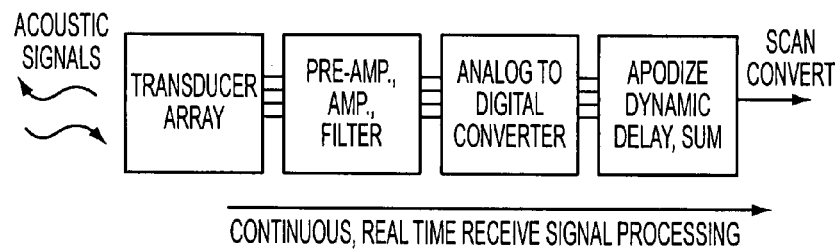
FIG. 4 schematically illustrates a block diagram of the receive side of a conventional ultrasound B-scan imaging system FIG. 5 schematically illustrates a block diagram of the receive side and image processing side of an exemplary embodiment of the present invention ultrasound B-scan imaging system FIG. 6 schematically illustrates a cross-sectional slice for an embodiment the present invention 2D C-scan method.
Figure 5:
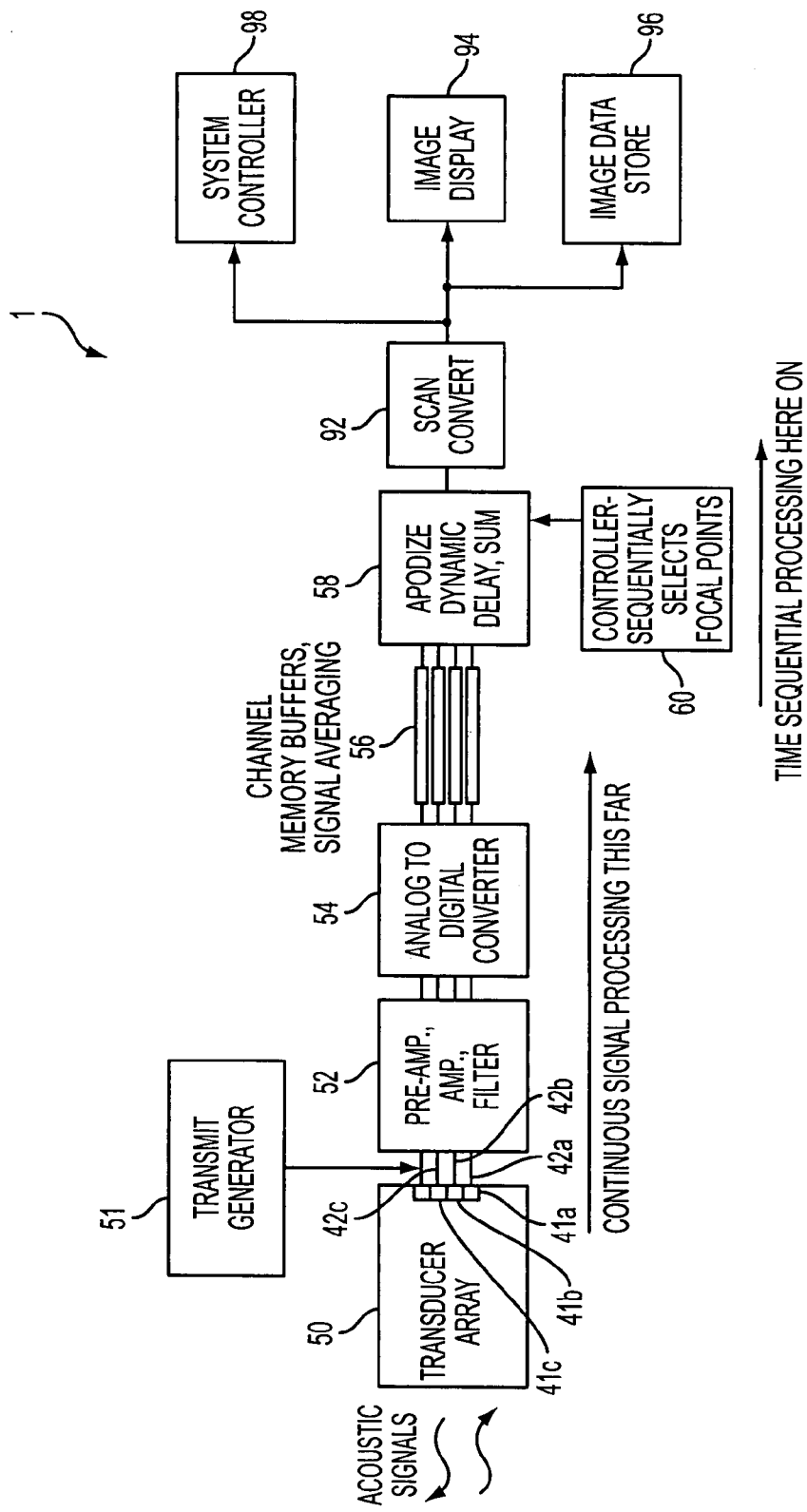

FIG. 4 illustrates a block diagram of the receive side of a conventional B-scan imaging system, while FIG. 5 illustrates the receive side of an exemplary embodiment of the present invention in communication with the processing side of the ultrasound system 1 as well. In conventional B-scan imaging, received signals are continuously processed, in real time, as they arrive to form a line of image data points per line firing cycle. In the exemplary embodiment of the present invention C-scan imaging system shown in FIG. 5, however, the signals for each active element are sequentially read out, instead of being read in 'real' signal propagation time, upon the collection of data in the memory buffers 56.

As schematically shown in FIG. 5, the ultrasound system 1 comprises a transmitter or generator 51. Every active element 41a, 41b, 41c, etc. (or at least a plurality of elements 41a, 41b, 41c, etc.) of the transducer array So in FIG. 5 can be connected to a corresponding array of individual transmitter or generator channels 42a, 42b, 42c, etc., which produces the relatively high transmit electronic signal for firing the piezoelectric element. In other embodiments of the invention, piezoelectric elements can be replaced with other electrical or pressure transducers, such as electrostatic devices, microelectromechanical systems (MEMS), and capacitor micro machined ultrasonic transducers (cMUTs). Moreover, every element location in the transducer array 50 is ideally active. Alternatively, an adequate compromise might be achieved with a degree of sparsity (i.e., unconnected elements in the transducer array). The nature of the sparsity may be either random or organized in some preferred arrangement (i.e., in a fully populated cross) or some mixture of random sampling and organized sampling (e.g. randomly sampled within a defined cross region). But whereas a sparse design produces adequate results at significant depths for a 3D based imaging system that outputs multiple 2D image planes, or 3D volumes, it should be appreciated that a sparse array will have varied effects for near field C-Scanning as envisioned here. Regardless, the present invention covers arrays for which all the elements are active and for which only a subset of elements is active.

Returning to FIG. 5, each active channel 42a, 42b, 42c, etc. that is in communication with the transducer array 50 is also connected to or includes a receive amplification system 52 for optimal signal conditioning. The amplification system 52 in an exemplary embodiment includes of a pre-amplifier, which is typically protected from the transmit voltage through a diode clamp circuit or equivalent. Additionally, the source impedance of the transmitter may be isolated from the transducer's receive signal by series diodes that only conduct during the high voltage transmit operation. After the first stage of amplification (which is typically a voltage follower or other very low noise amplification stage), the signal is then amplified by a programmed amount in order to make optimal use of the available range of subsequent circuitry.

It should be appreciated that the present invention imaging method is also applicable for selecting points that will lie on a plane that is not a c-scan and may be some alternate angle image plane. For example, it should be appreciated that the c-scan plane can be curved (rather than planar and parallel to the transducer surface), sloped, or skewed, or have finite thickness. Further, present invention imaging method is also applicable for focusing data through a small 3D volume.

Figure 8:
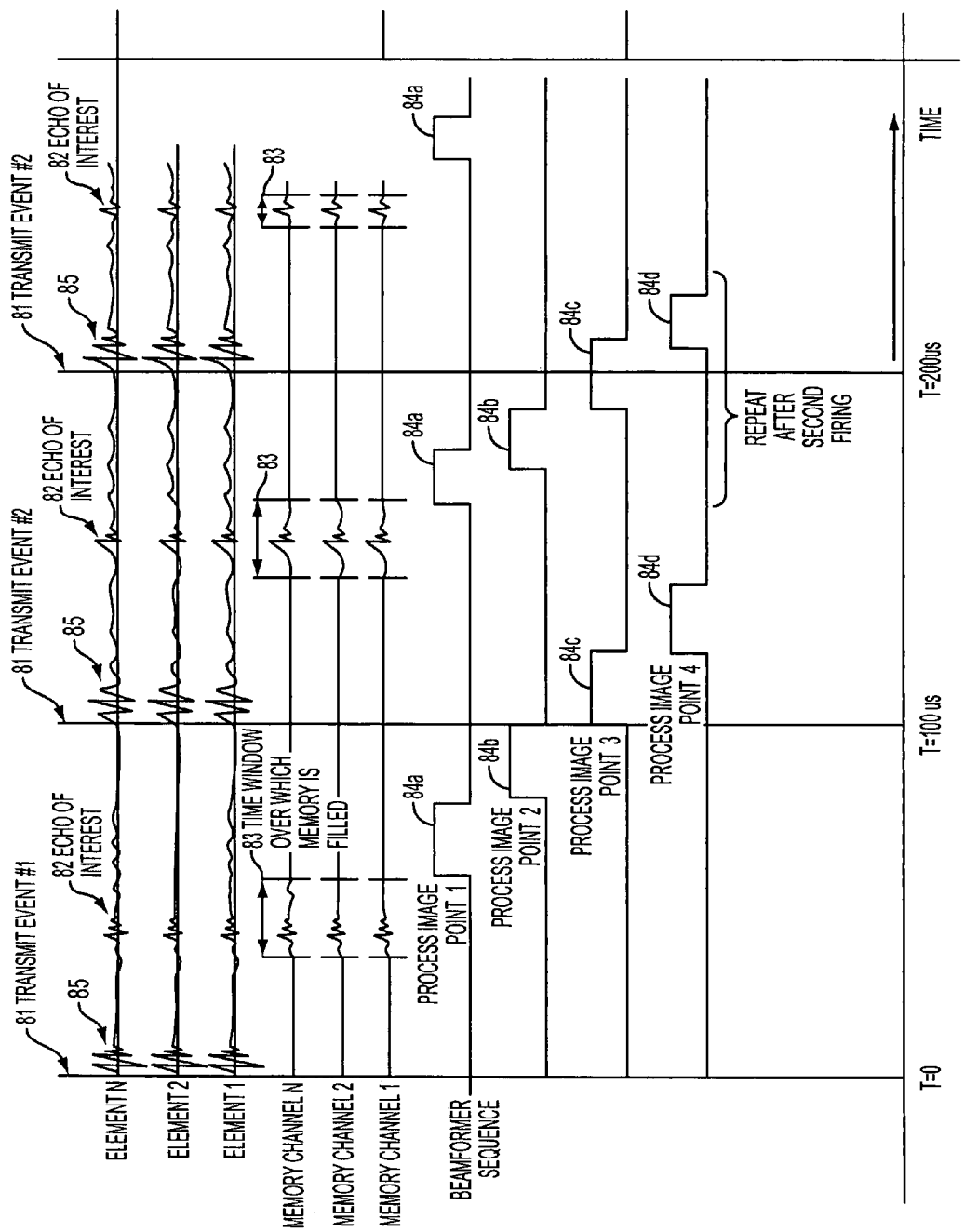
FIG. 8 is a timing diagram of the ultrasound signals of the active channels of an embodiment of the present invention ultrasound method.

Turning to FIG. 8, FIG. 8 represents a timing diagram of the ultrasound signals of the array of active channels 42a, 42b, 42c, etc. of an embodiment of the present invention ultrasound method. The system and method of an exemplary embodiment of the present invention periodically transmits 81 on all elements (1, 2, 3, . . . N) every 100 microseconds or as desired. Between these firings there is a big 'main bang' signal 85 immediately after transmit as the element 'dies down' followed by an evolution of echo signals from various depths. However, only a small time window 83 around the echo of interest 82 is of interest—that around the depth of interest. Therefore, although these practically continuous signals are present for all elements and all receive channels, the present invention system or method only saves data (for all channels) for a window 83 of time around that of interest. Once the data is collected, the present invention system or method uses the dead-time before the next gathering of good data during the process window 84 to process image points in a time in serial manner. Alternatively, the first processing step associated with the first image point can occur during the time window of image acquisition referenced as 83. In each processing step, the channel memory for each channel and time period of interest is operated with time delay specific to focusing required for the image point of interest. In this case as shown, four focusing (beamforming) operations are possible in each 100 microsecond interval. Thus, this exemplary embodiment of the present invention only need one fourth of the number of beamformers otherwise needed compared to conventional art. In completing of acquisition of echo data in time window 83 the processor sequentially processes image points 1, 2, 3, . . . N in sequential time windows 84a, 84b, 84c, etc. In this case, image point 84 does not start until completion of the time window 83. However, it is possible for the processing time window of the first data point 84a to be coincidental with time acquisition 83. Further, in addition to beamforming processing (such as compounding), other processing may occur within the window 84.

Returning to FIG. 5 for example, in one embodiment of the invention, the amplification system 52 also includes a filter in the analog processing stage to prevent aliasing effects due to high frequency components and to maximize the signal to noise ratio (SNR) by reducing random noise out of the desired band. The filter may be centered to pass either fundamental or harmonic data. Moreover, since the signals of interest for C-Scans are associated with a limited range, it is only strictly necessary to apply a fixed amount of gain, so that at the range (and associated time) of interest, the amplified signal is matched to the input of an analog to digital converter (ADC) 54, which is connected to or part of the channels 42a, 42b, 42c, etc. Additional precautionary steps can be taken to avoid saturation effects, or finite recovery saturation effects, if these are present. For example, in other embodiments of the invention the amplification system 54 employs time-varying gain to avoid the risks of saturation effects. Additionally, the ADC 54 may comprise a filter for selectively passing fundamental data. In an embodiment, a filter in the pre-sum stage allows filtering to be done once and data reused in all subsequent summing operations. Alternatively, filters can be applied on the beamformed (summed) data rather than on the pre-sum data where N filters are required (one for each element) instead of only one filter for the summed data. It should be appreciated that in one aspect a beamforming operation includes, but not limited thereto, a given or desired superset of delaying and summing channel data.

The ADC 54 produces a digital representation of the received analog signal. In digital systems, a signal from each sensor is first subjected to analog to digital conversion prior to beamforming provided by the Beamformer 58, as shown in the FIG. 5. In another exemplary embodiment, analog, instead of digital, processing may be employed. Beamforming was originally developed using analog signal processing. Networks of resistors were used to weight and sum the delayed signals in the beamforming process. However, the number of beams that can be implemented easily with such techniques is limited, since each beam requires many discrete delay lines, or delay lines with many different weighting networks. As a result, it became common to share a delay line through switches that sequentially scanned all directions. This approach, however, is limited to the availability of only one beam at any given time.

Advancements in integrated circuit electronics have provided capabilities for practical digital beamforming systems, which have reduced cost and processing power considerably. While digital hardware technology continues to improve rapidly, the full employment of digital beamforming processes is far from realized. For example, the majority of scanners today continue to operate from 1D arrays in producing 2D B-Scans. The 3D computational problems are compounded by the fact that since the speed of sound is sufficiently slow, it becomes essential to operate 16 or more receive beamforming processes in parallel to obtain the requisite beamformed line density and image frame rate (i.e., 30 frames/second). The present invention thus is not limited to any one type of data processing and embodies alternative approaches to the ADC and digital signal buffer components, such as CCD parts, which are essentially devices that store analog signals, and various hybrid systems of analog and digital processing.

The digital data in the embodiment of FIG. 5 is then stored in a memory buffer 56 on a per element basis. The memory buffer 56 is part of or is in communication with the plurality of channels 42a, 42b, 42c, etc. The digital element data is then read from the memory buffer 56 into the beamformer 58 on a time serial or time sequential basis, departing from the fully continuous 'real time' operation of the prior art systems.

Furthermore, since only a small depth range is actually needed to form the C-Scan, only a small time portion of the received echo signal need to be stored in the memory buffer. It should be appreciated that the memory can store an extended, full length signal record. It is simply the case here that most of that data would be of practically no value (unless utilized otherwise). Accordingly, the memory buffer 56 may be small in size, but still efficiently store multiple data points per line of firing for beamforming. Therefore, the present system allows for multiple data points per line of firing to be received by the beamformer 58 for multiple focusing operations.

In an embodiment, the beamformer 58 typically operates in a conventional manner and selects channels based on aperture design considerations for each received data point. The conventional functioning of the beamformer includes real-time operation, and thus the data transfer shifts from time sequential operation (during the memory buffer step) to continuous operation. Various beamforming techniques and focusing delays can be applied as desired to achieve the desired resolution. These include but are not limited to FIR filter-based sub sample interpolation, mixing to complex baseband (IQ) followed by phase rotation, and apodization. The beamformer can also be used to perform known Doppler operations such as: Spectral Doppler (PW), Color Velocity, Color Power, 'Doppler Tissue,' etc. The time taken to perform the focusing operation for one C-Scan image point is far less than the inter element firing delay, based on the assumption that the beamformer is capable of running at real time as conventional beamformers are. There is processing techniques associated with harmonic imaging of either tissue or contrast agents that may also be used with the present invention. These techniques include, but not limited thereto, coated transmit pulses, pulse inversion pairs, etc.

Additionally, digital shift registers are typically used to implement the beamforming delays, and digital multiplier components are used to implement weighting and summing the delayed signal data. The registers and multipliers are typically controlled by command signals generated in processors 60 that use various algorithms to compute the values of the delays and phase weightings necessary to achieve desired beam positions. Beam control for conventional digital systems thus still requires fairly complex data and signal processing, which is compounded by needs for more than one beam to be formed simultaneously. Thus, the efficiencies enabled by the present invention are important for achieving a sufficient density of active channels. Processing power is also greatly reduced in the various ways further discussed in other embodiments of the invention discussed throughout.

Still referring to FIG. 5, there is illustrated an exemplary embodiment of the imaging processing side of the system 1 including, for example, but not limited thereto a system controller 98 wherein the output of the beamformer 58 is supplied to a scan converter 92 which converts sector scan or other scan pattern signals to raster scan display signals. The output is supplied to an image display unit 94 and/or image storage/memory 96. The scan converted data can be displayed as an image of the regions of interest of the patient's body or other types of targets as desired or required.

Figure 6:
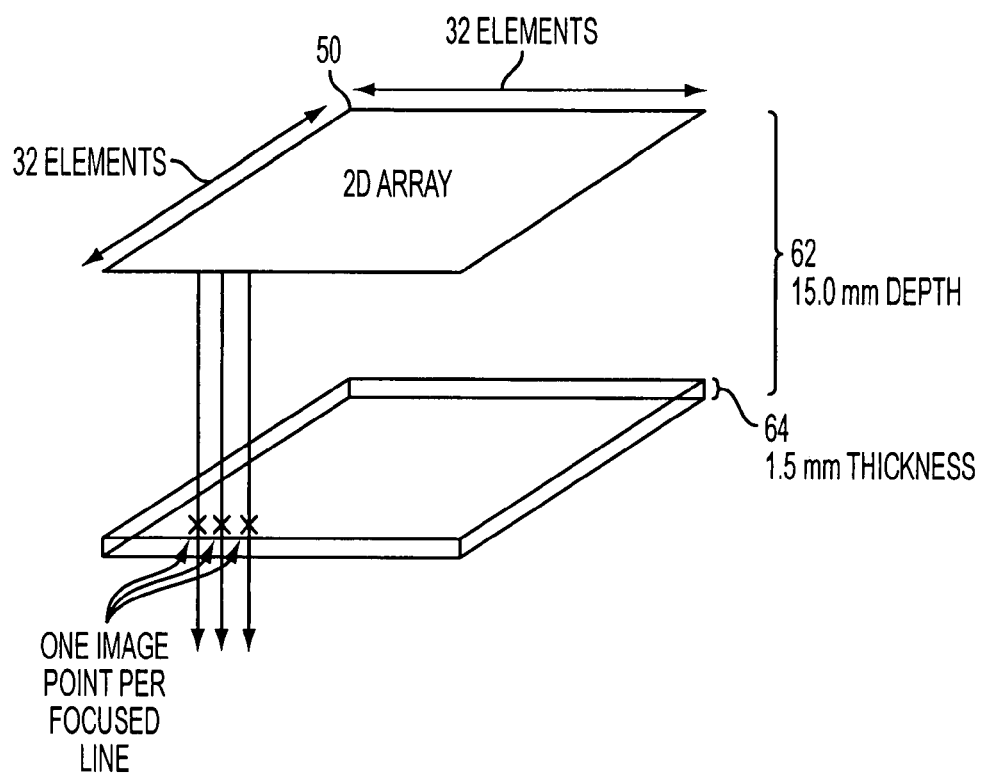

Next, an exemplary embodiment of the invention is illustrated in FIG. 6. In the example shown, the cross sectional 'slice' 62 required for the 2D C-Scan (the slice being perpendicular to the image display plane and transducer array) has a thickness of 1.5 mm is at a depth of 15 mm (62). The velocity of the signals is 0.75 mm/µs. Assuming that one line of firing signals "die out" at 30 mm, then the time between line firings is 30 mm/0.75 mm/µs, which is 40 µs. The time duration for the slice required for the C-Scan image would similarly be 1.5 mm/0.75 mm/µs, which is 2 µs (neglecting cosine theta effects of non-perpendicularly placed elements, such as elements other than at the center of the line). For beamforming operation, only 2 µs of the 40 µs would be used for imaging, leaving available 38 µs of every 40 µs of unused processing time between individual beamforming operations associated with a single point. This excess provides plenty of time to calculate beamformed image data for other points on the same line of firing. In particular, pertaining to this embodiment of the present invention, 38 µs of every 40 µs is available (i.e., excess time) between individual beamforming operations associated with a single point calculation for calculating beamformed image data for other points. This assumes that the time taken to form a single image point is limited by the duration of the digital data record being used. While this is true in regular 2D B-Scans, it is quite possible that faster beamforming processing will be achievable using the retrospective, limited depth data, operations being discussed herein. Thus the ability to calculate multiple image point values will be further enhanced by the sequential or time serial processing approach presented here.

In another exemplary embodiment of the present invention, the transmit signals are unfocused. Focused transmit signals will typically give better resolution, since using both transmit and receive focusing results in improved main lobe and lower sidelobe resolution. However, this approach necessitates a line of firing for every selected transmit focus point in the field, or for every active pixel in the display. As mentioned above, the number of individually fired lines could be on the order of 2,500 to 10,000 points. The present invention, however, enables a reasonable tradeoff to this excessive requirement by the use of an unfocused signal, or a plane wave, that simultaneously excites several active elements. A simultaneous excitation allows for a much simpler design. For example, in a conventional 2D transmit array of 32 by 32 (or 1024) fully active elements, all 1024 elements would need to be individually fired by focused transmit signals, to produce 1024 beamformed lines. The present invention would allow, on the other hand, a fully populated 2D transmit array of 1024 beamformed lines from many fewer unfocused (plane wave) transmit signals. It should be appreciated that the number of transmit signals required is a complex function of the number of array channels, number of desired image data points, proportion of 'dead time' over which beamforming operations can be made and speed at which each of these beamforming operations occur.

The different processing efficiencies gained by the present invention thus allows for the realization of a variety of cost reducing features. For example, the present invention also allows the receive echo signals to be recombined multiple times to create multiple focused image points for each line of firing. The per element signal delays are unaffected by the effects of differential transmit delays because the per element signal delays comprise only a part of the transmit delays that span each line of firing. This approach thus also allows for element signal averaging, which consists of summing the multiple focused image points for a given element and producing an averaged final image. Averaging can play a significant role in reducing the speckle and noise in acquired images.

Averaging techniques also provide significant advantages if the use of very low voltage electronics in transmit (such as about 3V or 5V) is desired. Even if higher voltages are used, the small elements used in high frequency arrays produced relatively small and noisy signals at the best of times and signal averaging improves overall performance by increasing maximum useful imaging penetration. Additionally, by using averaging techniques and circuits, smaller signals can be used which allow for shorter dead times (while waiting for echoes from greater depths to 'die out') between successive line firings. Alternatively, the improved SNR obtained when averaging is employed permits the use of higher frequencies (and higher resolution), which otherwise would be impractical.

In an exemplary embodiment of the invention that employs averaging, the memory buffer accumulates and averages successive data sets acquired from subsequent line firings. Averaging may require storing multiple records that each correspond to individual firings so that only the chosen signals (i.e., the 16 most recently fired signals) are available for averaging. Alternatively, an infinite impulse response (IIR)-type response may be employed, combining only the most recently acquired signal with a scaled version of the recursively accumulated previous signals. For example, ⅛ of the current signal may be combined with ⅞ of the recursively accumulated previous signals. Using reciprocal power of two based coefficients allows for efficient binary operations based on register shifting and summing.

It is useful to reiterate the time-saving advantages provided by the present invention, which may include the above-mentioned averaging techniques. The advantage of beamforming multiple points for each line of firing enabled by the present invention assumes that the time taken to form a single image point is limited by the duration of the digital data record being used. While this limitation may be an impediment for regular 2D B-Scans, it is now provided that faster beamforming processing is achievable using the retrospective, limited depth data just discussed.

It was also already mentioned that the size of the memory devices may be small. Small device features can also be realized by the of use of averaging operations, which can permit a smaller and low powered ADC to be used than would be required without averaging. For example, in one embodiment of the invention, a 10 bit device for the ADC may be required without averaging, whereas in other embodiments, 8 bits, or 6 bits may be required using the averaging technique. The present invention thus enables efficient reductions in cost and hardware dimensions.

Figure 7:
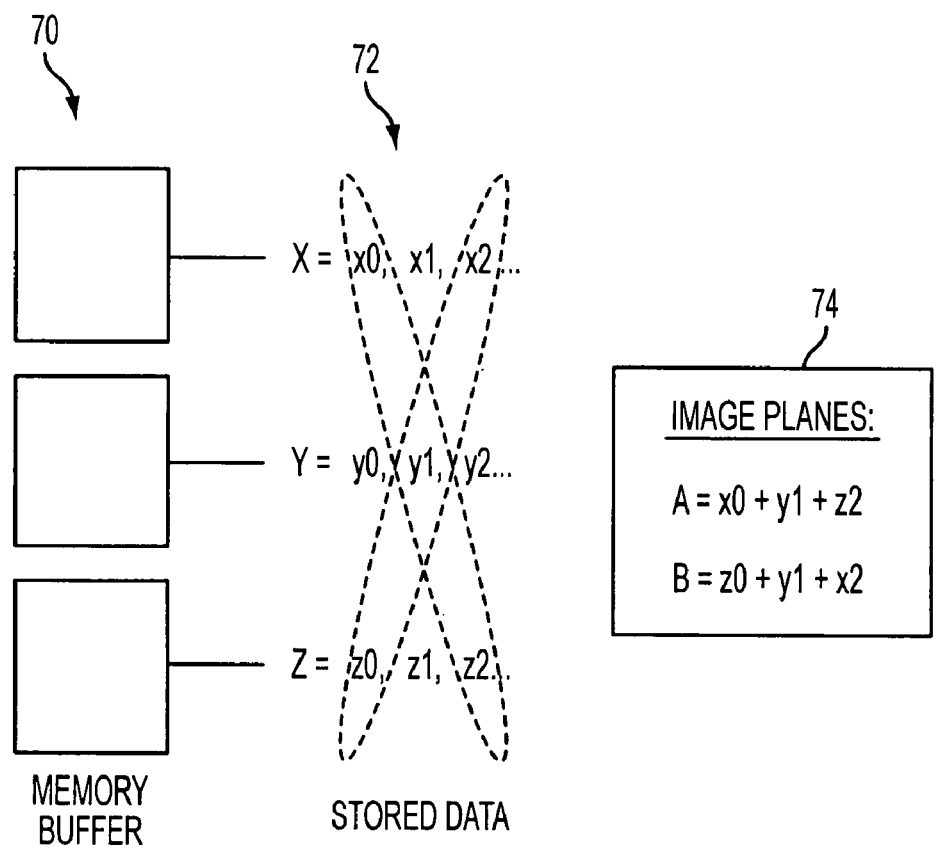
FIG. 7 schematically shows the imaging of different planes enabled by an embodiment of the present invention 2D C-scan beamformer method.

In another embodiment of the invention, the memory buffers that store multiple points per line of firing for each active element enable the imaging of 2D 'slices' at different angles. FIG. 7, which schematically shows the stored data 72 in memory buffers 70, illustrates this process. FIG. 7 shows that the memory buffer for element X has stored image data points $x_0, x_1, x_2, \ldots$, that the memory buffer for element Y has stored image data points $y_0, y_1, y_2, \ldots$, and that the memory buffer for element Z has stored image data points $z_0, z_1, z_2, \ldots$, for a given part of the array. The use of memory buffers according to the present invention would enable the display of images on planes 74 with different angles of incidence, such as image plane A, which consists of image points $x_0+y_1+z_2$. Similarly, the image plane B, which consists of points $x_2+y_1+z_0$, may be displayed. While imaging slices at different angles is possible for B-Scan technology, very large processing power is normally dissipated. The sequential or time serial reading process and reductions in hardware and processing enabled by the present invention allows for this kind of imaging at various angles to be facilitated efficiently.

In summary, the present invention provides a beamforming system and method for forming 2D C-scan images from 2D transducer arrays that result in approximately one order of magnitude reduction in processing complexity as compared to conventional systems and methods. The reduction in complexity translates to potentially lower cost and size, and enhanced resolution, processing power, imaging capabilities and commercial viability.

The following U.S. Patents and Applications are hereby incorporated by reference herein in their entirety:

U.S. Pat. No. 4,624,143 to Green, entitled "Ultrasonic Reflex Transmission Imaging Method and Apparatus With External Reflector;"

U.S. Pat. No. 4,880,010 to Szilard, entitled "Method of and Apparatus for Ultrasonic Imaging;"

U.S. Pat. No. 5,065,763 to Green et al., entitled "Combined Reflection and Transmission Untrasonic Imaging Method and Apparatus;"

U.S. Pat. No. 5,172,343 to O'Donnell, entitled "Aberration Correction Using Beam Data From a Phased Array Ultrasonic Scanner;"

U.S. Pat. No. 5,253,530 to Letcher, III, entitled "Method and Apparatus for Reflective Ultrasonic Imaging;"

U.S. Pat. No. 5,396,890 to Weng, entitled "Three-Dimensional Scan Converter for Ultrasound Imaging;"

U.S. Pat. No. 5,533,401 to Gilmore, entitled "Multizone Ultrasonic Inspection Method and Apparatus;"

U.S. Pat. No. 5,720,708 to Lu et al., entitled "High Frame Rate Imaging With Limited Diffraction Beams;"

U.S. Pat. No. 5,897,501 to Wildes et al., entitled "Imaging System With Multiplexer for Controlling a Multi-Row Ultrasonic Transducer Array;"

U.S. Pat. No. 5,902,241 to Seyed-Bolorforosh et al., entitled "Large-Aperture Imaging Using Transducer Array With Adaptive Element Pitch Control;"

U.S. Pat. No. 6,111,816 to Chiang et al., entitled "Multi-Dimensional Beamforming Device;"

U.S. Pat. No. 6,183,419 B1 to Wildes, entitled "Multiplexed Array Transducers With Improved Far-Field Performance;"

U.S. Pat. No. 6,234,025 B1 to Gieske et al., entitled "Ultrasonic Inspection Apparatus and Method Using a Focused Wave Device;"

U.S. Pat. No. 6,293,914 B1 to Sumanaweera et al., entitled "Ultrasonic System and Method for Measurement of Fluid Flow;"

U.S. Pat. No. 6,602,194 B2 to Roundhill et al., entitled "Dual Beamformer Ultrasound System for 2D and 3D Imaging;" and U.S. Pat. No. 6,692,439 to Walker et al., entitled "Angular Scatter Imaging System Using Translating Apertures Algorithm and Method Thereof," filed Jun. 3, 2002, of which is assigned to the present assignee.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. An ultrasonic imaging system capable of producing C-mode images and/or collecting 3D image data of a target, said system comprising:
    a two-dimensional transducer array comprising a plurality of elements that transmits and receives ultrasound signals;
    a plurality of processing channels, wherein said plurality of processing channels receive said receive ultrasound signals and generate channel signal samples;
    a storage device for receiving and storing a set of channel signal samples from the plurality of processing channels; and
    a beamforming device that receives said stored sets of channel signal samples in a time serial manner from said storage device, wherein the beamforming device performs multiple data-reading cycles to read the sets of channel signal samples multiple times per transmit firing event, and responsively forms at least one focused image point per data-reading cycle, the focused image points arranged on a C-scan plane.

2. The system of claim 1, wherein at least some of said processing channels comprises an amplifier.

3. The system of claim 2, wherein said amplifier comprises a pre-amplifier.

4. The system of claim 1, wherein at least some of said processing channels comprise a converter means for converting said received ultrasound signal from analog to digital data to generate said channel signal samples.

5. The system of claim 4, wherein said converting means includes a filter that selectively passes fundamental data.

6. The system of claim 4, wherein said converting means comprises a filter that selectively passes harmonic data.

7. The system of claim 1, wherein at least one of said ultrasound signals is a focused signal.

8. The system of claim 1, wherein at least one of said ultrasound signals is an unfocused plane wave that transmits signals simultaneously to more than one of said elements.

9. The system of claim 1, wherein said transducer array is a piezoelectric array.

10. The system of claim 1, wherein said transducer array is a non-piezoelectric array, including but not limited to at least one of electrostatic array, CMUT device, or MEMS device.

11. The system of claim 1, wherein said beamforming device is in communication with registers for shifting and summing at least some sets of channel signal samples that it receives.

12. The system of claim 1, wherein said storage device accumulates data from successive lines of signals.

13. The system of claim 1, wherein the storage device averages data from successive lines of signals.

14. The system of claim 1, further comprising:
    a scan converter for receiving output from said beamformer; and
    an image display unit and/or image storage unit.

15. The system of claim 1, wherein said beamforming device focuses separately each data point of said data that it receives.

16. An ultrasonic imaging method capable of producing C-mode images and/or collecting 3D image data of a target, said method comprising:
    transmitting and receiving ultrasound signals;
    storing said receive ultrasound data; and
    receiving said stored data in a beamforming device in a time serial manner, wherein said data is received and beamformed more than once per transmit firing event and forms multiple focused points arranged on a C-scan plane.

17. The method of claim 16, wherein the step of transmitting ultrasound signals comprises transmitting a focused signal.

18. The method of claim 16, wherein the step of transmitting ultrasound signals comprises transmitting an unfocused plane wave.

19. The method of claim 16, wherein the step of storing said signals further comprises accumulating data for successive lines of signals.

20. The method of claim 16, wherein the step of storing said signals further comprises averaging data for successive lines of signals.

21. The method of claim 16, wherein the step of receiving said serial data further comprises recombining data more than once for successive lines of signals.

22. The method of claim 16,
    scanning output from said beamformer; and
    displaying an image of at least a region of the target and/or storing image data of at least a region of the target.

23. The method of claim 16, wherein the beamforming comprises at least one of, but is not limited to, FIR filter-based interpolating, mixing to complex basebands, rotating phases, or apodizing.

24. The method of claim 23, wherein the beamforming is separately applied for each said stored data.

25. The method of claim 23, wherein the step of receiving said signals comprises receiving data that are stored on different planes.

26. The method of claim 16, wherein the step of transmitting and receiving ultrasound signals is performed on a two-dimensional transducer array.

27. The method of claim 26, wherein said two-dimensional transducer array comprises a plurality of elements.

28. The method of claim 16, wherein the step of storing receive ultrasound signals is performed on an array of processing channels.

29. The method of claim 28, wherein said array of processing channels comprises a storage device.

* * * * *